United States Patent [19]

Tarpley, Jr.

[11] 4,234,432

[45] Nov. 18, 1980

[54] POWDER DISSEMINATION COMPOSITION

[75] Inventor: William B. Tarpley, Jr., West Chester, Pa.

[73] Assignee: Energy and Minerals Research Co., Kennett Square, Pa.

[21] Appl. No.: 845,683

[22] Filed: Oct. 26, 1977

[51] Int. Cl.$^3$ .............................................. A62D 1/00
[52] U.S. Cl. ........................................ 252/8; 169/47; 252/2; 252/3; 252/7; 252/316; 252/317
[58] Field of Search .................... 252/2, 3, 7, 8, 316, 252/317; 169/47

[56] References Cited

U.S. PATENT DOCUMENTS

| | | | |
|---|---|---|---|
| 3,051,652 | 8/1962 | Olandt | 252/7 X |
| 3,267,030 | 8/1966 | Dessart | 252/2 X |
| 3,574,135 | 4/1971 | Sampson et al. | 252/317 |
| 3,654,105 | 4/1972 | Chilton et al. | 252/317 X |
| 4,042,521 | 8/1977 | Dunn | 252/7 X |

FOREIGN PATENT DOCUMENTS 1349508  4/1974  United Kingdom ..................... 252/8

OTHER PUBLICATIONS

Schneiderwirth et al., Journal of the American Pharmaceutical Association, Scientific Ed., vol. XXXVI, No. 12, Dec. 1947, pp. 402 to 406.

*Primary Examiner*—Leland A. Sebastian
*Attorney, Agent, or Firm*—Seidel, Gonda, Goldhammer & Panitch

[57] ABSTRACT

A composition of matter for use with disseminating apparatus comprising powder having at least a bimodal particle size distribution, a gelled liquid, the powder being substantially insoluble in the gelled liquid. Preferably, a liquefied gas forms at least a portion of the gelled liquid.

21 Claims, No Drawings

POWDER DISSEMINATION COMPOSITION

BACKGROUND OF THE INVENTION

The present invention relates to a composition for disseminating fine powders. Finely divided powders have found important uses in connection with fire extinguishers, pesticides, medicinal and cosmetic products, etc. This invention is broadly applicable to any of these products, but will be illustrated with reference to fire extinguishing agents.

A major problem in connection with disseminating conventional powder dissemination compositions has been the packing and clogging of the powders. In particular, conventional powder dissemination compositions are subject to the settling of finely divided powder particles which form masses. The settled powder masses are difficult to break up and tend to clog feed pipes, valves, nozzles and other parts of the apparatus used to disseminate the particles.

Another disadvantage of conventional finely divided powder dissemination compositions has been the relatively high volume occupied by the finely divided powders which have a unimodal particle size distribution. The interstitial spaces between the powder particles occupy a large proportion of the total volume of the total composition. This has resulted in relatively small weight capacities per unit volume for the powder dissemination composition.

In addition, the powder particles of conventional powder dissemination compositions have a tendency to agglomerate or sinter. This causes difficulties in terms of discharge of the powders and makes it necessary to add means for deagglomeration of the agglomerated or sintered powders. This is often difficult and sometimes impossible. As a result, it is often necessary to avoid using very fine particles, such as in the micron size range, which effectively form a cloud to smother a fire.

Another problem with prior art compositions occurs when it is desired to use more than one type of powder in the composition but it is not possible to mix them because they react with each other. This problem would occur, for example, when it is desired to use bicarbonates with acid phosphates.

The present invention is clearly distinguishable from conventional powder dissemination compositions and is an improvement over the composition disclosed in U.S. Pat. No. 3,402,665 of Tarpley, Jr. et al., which is believed to be the closest prior art. The patent discloses a non-pyrotechnic disseminator wherein the material to be disseminated may comprise finely divided powders suspended within a gelled liquid which comprises at least a portion of liquefied gas. There is no mention in the patent that the powders have any particular particle size distribution. Accordingly, the composition of the present invention has a distinct advantage over the patented composition due to the higher weight to volume ratio made possible by utilizing powders having at least a bimodal particle size distribution.

SUMMARY OF THE INVENTION

The present invention comprises a powder dissemination composition in which the powder is contained in a thixotropic gel which prevents the agglomeration, sintering and packing of the powder material.

The present invention comprises a composition of matter for use with disseminating apparatus comprising finely divided powder having at least a bimodal particle size distribution, a gelled liquid, the powder comprising about 30 to about 70 volume percent of the composition and being substantially insoluble in the gelled liquid. Preferably, a liquefied gas forms at least a portion of the gelled liquid.

The powder particles preferably have an average approximate maximum dimension between about 0.01 and about 100 microns. The yield stress of the composition need only be sufficiently high to prevent settling and agglomeration of the particles.

The compositions according to the present invention having the same effectiveness as conventional powder dissemination compositions occupy a volume of only about ⅓ to about 1/10 of conventional compositions. Compositions according to the present invention have an effectiveness equivalent to conventional compositions having about 2½ to about 4 times the weight of the present composition. Thus, a high weight to volume ratio makes the present compositions more effective than conventional compositions. This is particularly important when the compositions are used with disseminating apparatus having a small volume, for example, fire extinguishers intended for use in the home or with vehicles.

The advantages of the present invention are obtained by providing powders having at least a bimodal particle size distribution in a gelled liquid which may partially or totally comprise a liquefied propellant gas. By using a powder having at least a bimodal particle size distribution, the smaller particles tend to fill the interstitial spaces between the larger particles. This results in a more dense composition having a higher concentration of powder particles than conventional compositions which generally have a unimodal particle size distribution.

DESCRIPTION OF THE PREFERRED EMBODIMENTS

Although the present invention is applicable to the broad field of powder disseminating technology, it will be described in more detail with particular reference to the use of powder dissemination composition as fire extinguishing agents. Any modifications which may be necessary in applying the present invention to other technologies may be readily determined by those skilled in the powder disseminating art.

The present invention has maximum utility as a fire extinguishing agent with powder whose average approximately maximum dimension is between about 0.01 micron and about 100 microns. The powder particles may be equiaxed and relatively free from jagged edges or corners. In some instances, flaked particles may be desirable, such as flaked mica. Other desirable shapes for the particles include fibers, needles or lacy crystals.

The powder should have at least a bimodal particle size distribution. By incorporating in the present composition a powder having multimodal particle size distributions, a maximum amount of powder may be incorporated into a given volume of the composition. The smaller particles should be present in such quantity and size range to fit into the interstitial spaces between the larger particles as they pack together.

Where the powder has a bimodal particle size distribution, the larger particles of approximately uniform size will have interstices between the points at which the particles contact each other. Smaller particles may be packed in these interstices. In powders having a trimodal particle size distribution, the spaces between the larger particles and the smaller particles in the interstices of the larger particles may be packed with still smaller particles. It is preferred that the larger powder particles have an average approximate maximum dimension about 4 to about 10 times greater than the average approximate maximum dimension of the next smaller powder particles.

In a bimodal system, for example, if the larger powder particles have an average approximate maximum dimension of 100 microns, the smaller particles to be packed in the spaces between the larger particles would have an average approximate maximum dimension of between about 10 to about 25 microns. In a trimodal system, for example, where the largest powder particles have an average approximate maximum dimension of 100 microns, the next smaller particles would have an average approximate maximum dimension of about 10 to about 25 microns and the smallest particles would have an average approximate maximum dimension between about 1 and about 6.25 microns. Thus, it should be readily appreciated that the limiting factor in the number of particles having different sizes which may be present in a powder having a multimodal particle size distribution is determined by the ability to control particle size.

The composition of the present invention comprises from about 30 to about 70 volume percent of the powder, the remainder being gelled liquid. Normally, there is no advantage in having the powder percentage below about 30 volume percent, since the desired properties of the composition are to a large degree dependent upon the amount of powder present in the composition. Generally, the flow properties and handling characteristics of the composition may be adversely affected when the powder is present in greater than about 70 volume percent. The powder should be substantially insoluble in the gelled liquid.

The chemical nature of the powders to be used in the composition of the present invention will vary depending upon the intended use of the invention. Unlike prior dry powder dispensing compositions, it is not necessary to include flow promoting additives and anti-agglomerants in the finely divided powders of the present invention. Thus, because of the characteristics of the present invention, no useful purpose is served by the addition of such flow promoting additives and/or anti-agglomerants.

By way of example, when the composition of the present invention is intended for use as a fire extinguisher, the following exemplary materials may be used as the powder component: potassium bicarbonate, flake and expanded mica, sodium bicarbonate, boric acid, ammonium hydrogen phosphate, borax, potassium bromide, potassium chloride, borax-boric acid mixtures, strontium bromide, ammonium bicarbonate, ammonium pentaborate, ammonium bromide, tetrabromophthalic anhydride, tetrabromobisphenol, iodoform, etc.

In general, any powder capable of being produced in at least biomodal particle size distributions is contemplated by the present invention. The characteristics of the powder generally tend to define the characteristics of the composition.

The present invention includes the optional use of mixtures of powders. Thus, for particular purposes where it is desirable to confer multiple properties to a composition for a particular situation, the powders may be blended, such as by dry blending prior to being admixed in the compositions of the present invention. A significant advantage of the present invention is that mixtures of powders may be stored together as part of the composition. This is generally not feasible in dry mixes due to the packing, agglomeration and sintering of the particles. Normally interactive powders, such as bicarbonates and acid phosphates may be stably mixed and stored together as part of the present composition, since the gelled liquid separates the interactive powder particles.

The powder component of the present invention is mixed with a gelled liquid. As used herein, "gelled liquid" means a gelable liquid with a sufficient amount of gelling agent to form a composition having a yield stress sufficiently high to prevent settling and agglomeration of the powder particles. A yield stress of at least 20 dynes per square centimeter is adequate. A liquefied gas preferably comprises at least a portion of the gelled liquid.

The function of the gelled liquid is to keep the particles making up the finely divided powder from adhering to each other, as by sintering or by Van der Waals attraction, and from interacting with each other. The gelled liquid also serves to enhance the desired properties of the finely divided powder component, as by a synergistic action, or by a spreading or sticking action. Alternatively, the gelled liquid may serve as a diluent for the liquefied gas, so as to selectively modify the propellant properties of the liquefied gas.

Suitable gelable liquids include, for example: water, and nonaqueous liquids such as, tetrafluorodibromoethane, chlorobromomethane, carbon tetrachloride, tris (2, 3-dibromopropyl) phosphate, ethylene bromide, diethylpyrophosphate, glycerine, etc.

The liquefied gas may form at least a portion of the gelled liquid, and in some embodiments, all of the gelled liquid may comprise a liquefied gas. The relative proportion of liquefied gas to the remainder of gelled liquid depends upon the physical properties of the liquefied gas and of the gelled liquid, as well as the characteristics of the powder and intended use of the composition. For example, when the composition is used to form a cloud, as in extinguishing the flame front of an explosion, the gelled liquid is preferably comprised almost totally of the liquefied gas. Where fire in an engine compartment is to be extinguished by a composition conveyed through ducts and valves, or when a hand-held extinguisher is used, the liquefied gas may comprise less of the composition.

Where the liquefied gas is relatively highly volatile, i.e., where it has a relatively high vapor pressure, the portion of the gelled liquid which consists of liquefied gas may be relatively small, such as of the order of about 5 weight percent of the total composition.

Compositions wherein all of the gelled liquid comprises a liquefied gas have primary utility where the liquefied gas is one having a relatively low volatility, where a high propellant force is needed for a particular use, or where the liquefied gas has the property of augmenting the functionality of the finely divided powder, as in the case of liquefied halogenated gases being used in a fire extinguisher.

Examples of liquefied gases which may be used in the gelled liquid component of the compositions according to the present invention are: trifluorobromomethane, perfluoropropane, perfluorocyclobutane, dichlorodifluoromethane, ammonia, tetrafluoromethane, methyl bromide, trifluoromethane, trifluorochloromethane, hexafluoroethane, difluorochloromethane, etc.

The compositions of the present invention include a gelling agent in an amount sufficient to effect gelling of all of the liquid present in the composition. The gelling agent should have a gelling efficacy so as to comprise no more than about 5 weight percent of the composition. In some compositions, the powder component possesses gelling characteristics, so that the amount of gelling agent which need be present in such compositions may be reduced. Generally, at least about ½ weight percent of the composition should be gelling agent to achieve satisfactory gelling of the liquid portion of the composition.

Suitable gelling agents include, for example: pyrogenic silica derived from the combustion of silicon tetrachloride, such materials being commercially available as gelling agents under the trademark "Cab-O-Sil"; carbon black having a clean microsurface and a high degree of structure with the structure being internal with particles smaller than 25 millimicrons as measured by an electron microscope and presenting a ratio of BET surface as determined by nitrogen adsorption measurement to electron microscope surface of between 2½ and 6 and with larger particles being external, namely possessing persistent particular chain formation observable in the electron microscope after mulling by the procedure of Ladd, *Rubber Age*, Vol. 57, June 1945, p. 299; pyrogenic aluminum oxide derived from the combustion of aluminum trichloride; pyrogenic titanium dioxide derived from the combustion of titanium tetrachloride; aluminum or magnesium salts of fatty acids such as stearate, palmitate, octoate or mixed fatty acids primarily oleate (Alumagel); colloidal attapulgite clay; colloidal quaternized bentonite; sub-micron magnesium oxide; sub-micron potassium bicarbonate, and the like.

In some situations, a surfactant may be added to improve wetting of the finely divided powders. Although generally not necessary, where a surfactant is desired, it should be present in a concentration of about 0.1 to about 1 weight percent based on the amount of gelled liquid in the composition. Suitable surfactants include, for example: sorbitan trioleate, polyethylene glycol ether of hydroabietyl alcohol, polyoxyethylene sorbitan monooleate, diethylene glycol laurate, sulfonated castor oil, triethanolamine monooleate, etc.

The compositions of the present invention are kept within standard containers having a structural strength sufficient to withstand the pressures developed under storage and use temperatures. Generally, these pressures will be of the order of 15 to 250 p.s.i.g. at room temperature. Suitable containers include any of the standard pressurized fire extinguisher containers as well as the containers disclosed in U.S. Pat. No. 3,402,665 of Tarpley, Jr., et al.

The invention will now be described in more detail with reference to the following specific non-limiting examples. In preparing the compositions according to the present invention, all of the ingredients may be mixed together in a pressurized high shear mixer at ambient temperature to avoid evaporation of volatile liquids or of the liquefied gas. Alternatively, the gelling agent can be added to the normally liquid constituent and subjected to high shear mixing followed by chilling to the liquefaction temperature of the liquefied gas. The liquefied gas is then admixed with the gelled liquid at atmospheric pressure. The other ingredients can then be added to the chilled mixture to form the composition which is used to fill the disseminating container.

Examples 1-5 illustrate compositions according to the present invention wherein the powders have a bimodal particle size distribution and wherein the powder component is present in an amount of about 30 to about 70 volume percent.

EXAMPLE 1

| Component | Average Approximate Maximum Dimension (μ) | Parts by Weight |
|---|---|---|
| Sodium Bicarbonate | 40 | 40 |
| Sodium Bicarbonate | 8 | 15 |
| Trifluorotrichloroethane | | 35 |
| Trifluorobromomethane | | 8.5 |
| Pyrogenic Silica | | 1.5 |

EXAMPLE 2

| Component | Average Approximate Maximum Dimension (μ) | Parts by Weight |
|---|---|---|
| Potassium Bicarbonate | 35 | 50 |
| Potassium Bicarbonate | 5 | 13 |
| Chlorodifluoromethane | | 35 |
| Pyrogenic Alumina | | 2 |

EXAMPLE 3

| Component | Average Approximate Maximum Dimension (μ) | Parts by Weight |
|---|---|---|
| Potassium Bromide | 30 | 48 |
| Potassium Bromide | 6 | 10 |
| Dichlorodifluoromethane | | 7.2 |
| Trichlorotrifluoroethane | | 33.6 |
| Aluminum Octoate | | 1.2 |

EXAMPLE 4

| Component | Average Approximate Maximum Dimension (μ) | Parts by Weight |
|---|---|---|
| Potassium Chloride | 45 | 35 |
| Potassium Chloride | 12 | 10.8 |
| Trifluorobromomethane | | 7.8 |
| Dibromotetrafluoroethane | | 44.8 |
| "Thixcin" (a castor oil derivative) | | 1.6 |

EXAMPLE 5

| Component | Average Approximate Maximum Dimension (μ) | Parts by Weight |
|---|---|---|
| Tetrabromobisphenol A | 30 | 35 |
| Tetrabromobisphenol A | 6 | 5 |
| Perfluorocyclobutane | | 58 |
| Alumagel | | 2 |

Examples 6-10 illustrate compositions according to the present invention wherein the powder has a trimodal particle size distribution:

EXAMPLE 6

| Component | Average Approximate Maximum Dimension (μ) | Parts by Weight |
|---|---|---|
| Potassium Bicarbonate | 30 | 40 |
| Potassium Bicarbonate | 6 | 15 |
| Potassium Bicarbonate | 1 | 5 |
| Bromoform | | 39 |
| Pyrogenic Silica | | 1 |

EXAMPLE 7

| Component | Average Approximate Maximum Dimension (μ) | Parts by Weight |
|---|---|---|
| Strontium Bromide | 30 | 45 |
| Strontium Bromide | 6 | 10 |
| Strontium Bromide | 1 | 5 |
| Bromotrifluoromethane | | 4.8 |
| Dibromotetrafluoroethane | | 34.3 |
| Pyrogenic Silica | | 0.9 |

EXAMPLE 8

| Component | Average Approximate Maximum Dimension (μ) | Parts by Weight |
|---|---|---|
| Potassium Chloride | 45 | 35 |
| Potassium Chloride | 9 | 8 |
| Potassium Chloride | 2 | 2 |
| Perfluoropropane | | 53 |
| Acetylene black | | 2 |

EXAMPLE 9

| Component | Average Approximate Maximum Dimension (μ) | Parts by Weight |
|---|---|---|
| Potassium Bromide | 35 | 30 |
| Potassium Bromide | 7 | 10 |
| Potassium Bromide | 2 | 5.8 |
| Chlorodifluoromethane | | 7.8 |
| Trichlorotrifluoroethane | | 44.8 |
| Carbon Black (Royal Spectra) | | 1.6 |

EXAMPLE 10

| Component | Average Approximate Maximum Dimension (μ) | Parts by Weight |
|---|---|---|
| Ammonium Hydrogen Phosphate | 40 | 43.5 |
| Ammonium Hydrogen Phosphate | 8 | 10 |
| Ammonium Hydrogen Phosphate | 2 | 5 |
| Nitrous Oxide | | 40 |
| Pyrogenic Silica | | 1.5 |

Example 11 illustrates a composition according to the present invention comprising a mixture of different powders forming the powdered component:

EXAMPLE 11

| Component | Average Approximate Maximum Dimension (μ) | Parts by Weight |
|---|---|---|
| Potassium Bicarbonate | 30 | 20 |
| Potassium Bicarbonate | 6 | 5 |
| Potassium Bicarbonate | 1 | 1 |
| Ammonium Hydrogen Phosphate | 40 | 20 |
| Ammonium Hydrogen Phosphate | 8 | 5 |
| Ammonium Hydrogen Phosphate | 2 | 1 |
| Tetrafluorodibromoethane | | 30 |
| Trifluorobromoethane | | 17 |
| Pyrogenic Silica | | 1 |

The potassium bicarbonate in Example 11 generates carbon dioxide upon contact with high temperatures. The ammonium hydrogen phosphate forms a skin or adherent film upon contact with a burning fuel. Both of these materials form so-called chain breakers, namely materials which prevent the formation of a chain reaction, which results in the quenching of the flame. The mixture of potassium bicarbonate and ammonium hydrogen phosphate may be stored indefinitely in the gelled liquid forming the composition.

The compositions of the present invention may be sprayed or disseminated in any conventional manner. It is preferred that when the composition comprises a fire extinguishing agent, all components of the composition, individually and as mixed together to form the composition, be fire extinguishing agents, except the gelling agent and surfactant, when a surfactant is present. When the compositions of the present invention are used in a confined area, such as a mine, ship or other vehicle, or anywhere where people are likely to inhale or come in contact with the composition, the components of the composition, individually and together, generally should not be physiologically dangerous as disseminated and used under conditions normally encountered in extinguishing fires.

One presently preferred method of using a fire extinguishing composition in accordance with the present invention is to form a cloud of the composition in the vicinity of a fire or explosion to be extinguished. For example, dust and gas explosions in mines can be quenched by an adequate quantity of finely divided extinguishing agents and brominated liquefied gas ejected into the air just ahead of the flame front. Preferably, the composition is ejected automatically upon the happening of a predetermined condition, such as the presence of heat, smoke, concussion waves from an explosion, etc.

For a cloud-forming composition to be most effective, the particles must have a large surface area and remain suspended in the moving gas stream for a sufficient time that the flame front can catch up with the cloud of particles. The powder component of the composition should have a particle size distribution between about 1 to about 5 microns. Such a composition can only be ejected rapidly into a cloud of sufficient size and completely dispersed into individual particles by the use of a vaporizing gel which prevents particle agglomeration.

The cloud-forming compositions need not have the ability to flow at all, since they simply remain in the container until disseminated, usually by the bursting of the container by an explosive charge. The cloud size is controlled by varying the amount of liquefied gas in the composition and may readily be determined by those skilled in the art.

In another type of application, it is desirable to eject larger size particles, on the order of about 8 to 40 microns, from a distance into the flame front. The larger size particles are desirable because smaller, micron size particles tend to rapidly lose their velocity in air due to drag forces and generally cannot be projected long distances. Additionally, the larger particles fall more rapidly onto the combustible material to form a protective layer to prevent ignition and/or reignition.

The present invention may be embodied in other specific forms without departing from the spirit or essential attributes thereof and, accordingly, reference should be made to the appended claims, rather than to the foregoing specification as indicating the scope of the invention.

I claim:

1. A nonaqueous thixotropic composition of matter for use with disseminating apparatus comprising powder having at least a bimodal particle size distribution, a gelled liquid, the powder comprising about 30 to about 70 volume percent of the composition and being substantially insoluble in the gelled liquid.

2. A composition according to claim 1 wherein the powder has a bimodal particle size distribution whereby the larger powder particles have an average approximate maximum dimension about four to about ten times greater than the average approximate maximum dimension of the smaller powder particles.

3. A composition according to claim 1 wherein the powder has a trimodal particle size distribution whereby the larger powder particles have an average approximate maximum dimension about five to about ten times greater than the average approximate maximum dimension of the next smaller powder particles.

4. A composition according to claim 1 wherein the gelled liquid comprises a gelable liquid and a liquefied gas.

5. A composition according to claim 1 wherein the gelled liquid comprises a liquefied gas and a quantity of gelling agent sufficient to effect gelling of all of the liquefied gas.

6. A composition according to claim 1 wherein the composition has a yield stress of at least 20 dynes per square centimeter.

7. A composition according to claim 1 wherein the composition is pressurized at about 15 to about 250 p.s.i.g. at room temperature.

8. A composition according to claim 1 wherein the powder particles have an average approximate maximum dimension of about 0.01 to 100 microns.

9. A composition according to claim 1 wherein the composition is a fire extinguishing agent.

10. A composition according to claim 1 wherein the powder component comprises two different powdered materials.

11. A nonaqueous thixotropic composition of matter for use with disseminating apparatus comprising a powder having at least a bimodal particle size distribution within a range of about 0.01 to about 100 microns in average approximate maximum dimension, a gelled liquid, the powder being disposed within and substantially insoluble in the gelled liquid, the composition having a yield stress not less than about 20 dynes per square centimeter.

12. A composition according to claim 11 wherein the gelled liquid comprises a gelable liquid and a liquefied gas.

13. A composition according to claim 11 wherein the gelled liquid comprises a liquefied gas and a quantity of gelling agent sufficient to effect gelling of all of the liquefied gas.

14. A composition according to claim 11 wherein the gelled liquid comprises a liquefied gas and a gelling agent, the gelling agent comprising about one-half of one weight percent to about five weight percent of the composition.

15. A composition according to claim 11 wherein the gelled liquid comprises a liquefield gas, a quantity of gelling agent sufficient to effect gelling of all of the liquefied gas, and a surfactant, the surfactant comprising about 0.1 to about 1 weight percent of the gelled liquid.

16. A composition according to claim 11 wherein the powder comprises about 30 to about 70 volume percent of the composition.

17. A composition according to claim 11 wherein the powder particles having a shape selected from the group consisting of generally equiaxed grains, flakes, fibers, needles and lacy crystals.

18. A composition according to claim 11 wherein the composition is a fire extinguishing agent.

19. A composition according to claim 18 wherein the components generally are not physiologically dangerous as disseminated and used under conditions normally encountered in extinguishing fires.

20. A method of extinguishing a fire by forming a cloud of a composition according to claim 18 in the area of the fire.

21. A method of extinguishing a fire by forming a cloud of a composition according to claim 19 in the area of the fire.

* * * * *